US010466210B2

(12) United States Patent
Chen

(10) Patent No.: US 10,466,210 B2
(45) Date of Patent: **\*Nov. 5, 2019**

(54) POTTERY SHARD ANALYSIS USING MATCHING VIBRATION SIGNATURES

(71) Applicant: Baxton Chen, San Marino, CA (US)

(72) Inventor: Baxton Chen, San Marino, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 15/644,303

(22) Filed: Jul. 7, 2017

(65) Prior Publication Data

US 2017/0307570 A1 Oct. 26, 2017

(51) Int. Cl.
*G01N 29/44* (2006.01)
*G01N 29/12* (2006.01)
*E02F 9/26* (2006.01)

(52) U.S. Cl.
CPC ......... *G01N 29/4427* (2013.01); *E02F 9/261* (2013.01); *G01N 29/12* (2013.01); *G01N 2291/028* (2013.01)

(58) Field of Classification Search
CPC .................................................. G01N 26/4436
See application file for complete search history.

(56) References Cited

U.S. PATENT DOCUMENTS 4,530,246 A * 7/1985 Pitman ..................... G01N 3/00
73/644
2010/0089160 A1 * 4/2010 Cosentino ............... G01L 1/255
73/579
2016/0238486 A1 * 8/2016 Bense .................... G01M 15/12
2017/0052148 A1 * 2/2017 Estevez .................. G01S 15/10

OTHER PUBLICATIONS

Salazar, A. et al., Ultrasonic Non-Destructive Testing of Archaeological Ceramics. In 9th European Conference on NDT—Sep. 2006—Berlin (Germany). Retrieved Jan. 3, 2019, from https://www.ndt.net/article/ecndt2006/doc/P124.pdf.*
Archaeologists recover Iron Age pottery at site in Welford. (Jul. 1, 2016). Retrieved Jan. 4, 2019, from https://le.ac.uk/news/2016/january/archaeologists-recover-iron-age-pottery-at-site-in-welford.*

* cited by examiner

*Primary Examiner* — Peter J Macchiarolo
*Assistant Examiner* — Alexander A Mercado
(74) *Attorney, Agent, or Firm* — McDermott Will & Emery LLP

(57) ABSTRACT

A pottery shard analyzer may determine one or more characteristics of an unidentified pottery shard. A vibration injector may cause the unidentified pottery shard to vibrate with a vibration signature that is dependent on the one or more characteristics of the unidentified pottery shard. A vibration detector may detect and extract a vibration signature from the vibration of the unidentified pottery shard caused by the vibration injector. A vibration signature comparator may: compare the detected vibration signature of the unidentified pottery shard with vibration signatures of multiple identified pottery shards having one or more known characteristics; and flag one or more of the identified pottery shards that have vibration signatures that are similar to the vibration signature of the unidentified pottery shard.

21 Claims, 3 Drawing Sheets

POTTERY SHARD ANALYSIS USING MATCHING VIBRATION SIGNATURES

BACKGROUND

Technical Field

This disclosure relates to pottery shards and to a determination of their characteristics, including their age and/or the geographic location at which they were made.

Description of Related Art

The invention of pottery was a major step in human evolution. It usually has enough strength to protect food from vermin, enough liquid impermeability to store water and wine, and enough fire resistance to be used in cooking.

The earliest pottery was created about 20,000 years ago. Biological and metallic artifacts are prone to decomposition and corrosion. But ancient pottery shards often withstand the test of time and are often found in archeological sites. Due to evolving pottery making techniques over, pottery shards can often help archeologists date a particular excavation layer during excavation. Pottery can also help archeologists identify the geographic and cultural origins of a site, as each civilization often developed its own unique types of pottery.

Pottery shards are often classified by archeologists based on their color, surface texture, density, thickness, curvature, material, and shape. Since complete and intact potteries are rarely found, archeologists often have to extrapolate based on individual shards. The conclusions drawn are often incomplete and unsatisfactory.

Techniques have been developed to provide more accurate analysis. One example is pottery petroglyph. Thin sections (e.g., 30-microns) of the shards are examined under a polarized light microscope to see the inorganic elements as a way to estimate the soil origin of the pottery and thus its possible cultural source. Alternatively, organic residues have been harvested from the pottery for radioactive dating. Both of these techniques, however, may require extensive preparation in a laboratory and thus may not be feasible in the field.

What has long-since been needed is the ability to provide quick, real time analysis of pottery shards in order to guide field excavation.

SUMMARY

A pottery shard analyzer may determine one or more characteristics of an unidentified pottery shard. A vibration injector may cause the unidentified pottery shard to vibrate with a vibration signature that is dependent on the one or more characteristics of the unidentified pottery shard. A vibration detector may detect and extract a vibration signature from the vibration of the unidentified pottery shard caused by the vibration injector. A vibration signature comparator may: compare the detected vibration signature of the unidentified pottery shard with vibration signatures of multiple identified pottery shards having one or more known characteristics; and flag one or more of the identified pottery shards that have vibration signatures that are similar to the vibration signature of the unidentified pottery shard.

The vibration signature comparator may output the one or more characteristics of the flagged pottery shards.

The vibration injector may include an ultrasound transmitter and the vibration detector include an ultrasound receiver.

The vibration injector may cause the unidentified pottery shard to vibrate at multiple different frequencies either simultaneously or sequentially. The vibration detector may detect the vibration signature of the unidentified pottery at each of the multiple different frequencies. The vibration signature comparator may: compare the detected vibration signature of the unidentified pottery shard at each of the multiple different frequencies with vibration signatures of the multiple identified pottery shards at each of the multiple different frequencies; and flag one or more of the identified pottery shards that have vibration signatures at the multiple different frequencies that are each similar to the vibration signature of the unidentified pottery shard at the multiple different frequencies.

One of the characteristics may be the age of the pottery shard.

One of the characteristics may be the geographic location where the pottery shard was made. Another of the characteristics may be the age of the pottery shard.

The vibration signature comparator may use a correlation function to make the comparison.

The pottery shard analyzer may include a database of vibration signatures of the identified pottery shards.

The vibration signatures of the unidentified and identified pottery shards may be obtained under comparable conditions.

One of the comparable conditions may be the separation distance between the vibration injector and the pottery shard.

A method of excavating a first archeological site may include: extracting an unidentified pottery shard during the excavating having one or more unknown characteristics; using the pottery shard analyzer of claim 1 to determine the one or more unknown characteristics; and deciding whether the determined one or more characteristics warrant continued excavation at the first archeological site; if the determined one or more characteristics warrant continued excavation at the archeological site, continuing to excavate at the first archeological site; and if the determined one or more characteristics do not warrant continued excavation at the archeological site, not continuing to excavate at the first archeological site.

The method may include excavating at a second archeological site if the determined one or more characteristics do not warrant continued excavation at the first archeological site.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
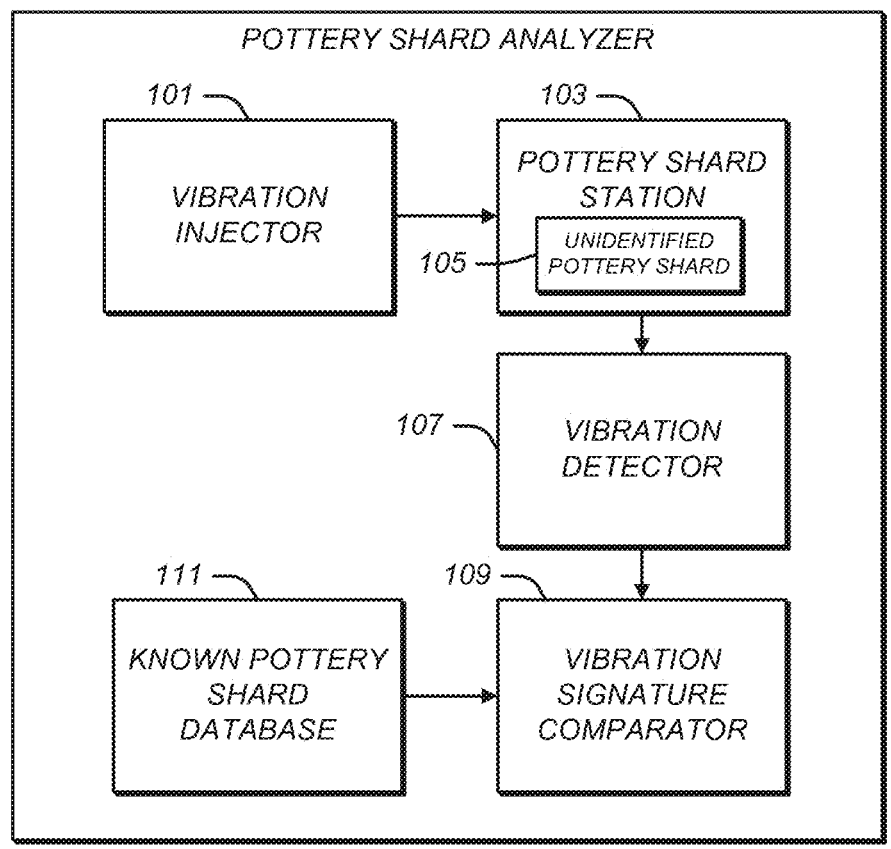
FIG. 1 illustrates an example of a pottery shard analyzer for determining one or more characteristics of an unidentified pottery shard.

FIG. 1 illustrates an example of a pottery shard analyzer for determining one or more characteristics of an unidentified pottery shard 105. As illustrated in FIG. 1, the pottery shard analyzer may include a vibration injector 101, a pottery shard station 103 for holding the unidentified pottery shard 105, a vibration detector 107, a vibration signature comparator 109, and a known pottery shard database 111.

The vibration injector 101 may be of any type. For example, the vibration injector may be a hammer, one or more tuning forks, an ultrasound generator, an electromagnetic source such as a microwave; an MRI (Magnetic Resonance Imaging) system, and/or any other type of vibration injection device.

Figure 2:
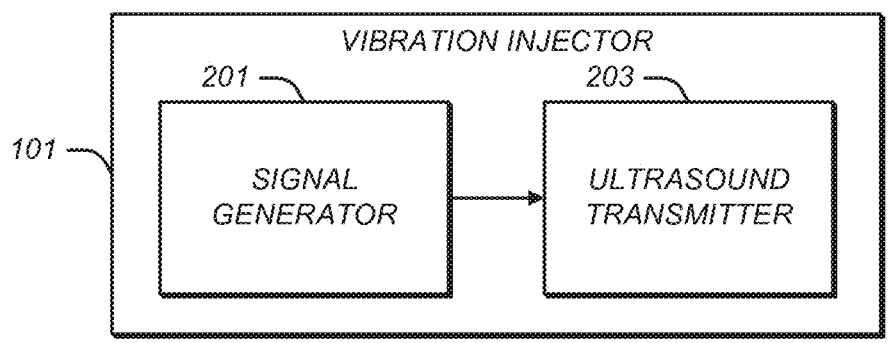
FIG. 2 illustrates an example of the vibration injector illustrated in FIG. 1 that generates and injects ultrasound.

FIG. 2 illustrates an example of the vibration injector 101 illustrated in FIG. 1 that generates and injects ultrasound. As illustrated in FIG. 2, the vibration injector 101 may include a signal generator 201 and an ultrasound transmitter 203.

The signal generator 201 may be any type of circuit or device that generates an ultrasound signal. The signal generator 201 may be configured to generate a signal at one or more ultrasound frequencies, such as at 3.5 MHz, 5 MHz, 7 MHz, and/or 10 MHz. The signal may be a sign wave or a wave of another shape that has harmonic content, such as a square wave. The signal may instead be noise. The signal may be artificially-generated or a recording of a natural sound, such as the buzzing of bees or ocean waves, or of any other origin The signal generator 201 may be configured to generate multiple different ultrasound frequencies, either simultaneously and/or serially.

The signal generator 201 may be portable or stationary. The signal generator 201 may be a circuit dedicated to generating the desired signal(s) or a portable or stationary general purpose computer programmed to generate the desired signal(s). A USB or other type of port may be used to deliver the generated signal(s) to the ultrasound transmitter 203.

The ultrasound transmitter 203 may be configured to generate ultrasound from the ultrasound signal(s) received from the signal generator 201 that faithfully replicates the received signal(s) as an ultrasound wave or waves. The ultrasound transmitter 203 may be a single or multi-frequency ultrasound transducer. The ultrasound transmitter 203 may be stationary or portable and may be configured to be help by hand or by a holding apparatus.

The ultrasound transmitter 203 may be configured to gently contact a surface of the unidentified pottery shard 105 to make it vibrate or to be at a fixed separation distance from it. The ultrasound transmitter 203 may be configured to be held by a mechanical holding device, such as a plyers, clasp, ring, tape, or other adhesive.

The pottery shard station 103 may be configured to hold the unidentified pottery shard 105. The pottery shard station 103 may be of any type. For example, the pottery shard station may be a human hand, a platform, a stand with a clamp configured to clamp the unidentified pottery shard 105 firmly in place, but gently enough to ensure that it is not damaged. The pottery shard analyzer may be configured such that the vibration injector 101 and the unidentified pottery shard station 103 are maintained in a fixed relation to one another, thereby eliminating variations in the separation distance between the vibration injector 101 and the unidentified pottery shard 105.

The vibration detector 107 may be configured to detect a vibration signature from the unidentified pottery shard 105 while it is vibrating under the influence of the vibration injector 101. The phrase "vibration signature" means the sound emitted by the vibration of the unidentified pottery shard 105 during a fixed period of time, such as for a period of 10 ms, 100 ms, or 1 sec. The vibration signature may be a faithful reproduction of the vibration of the unidentified pottery shard 105 under the influence of the vibration injector 101 or a processed version of that signal that has undergone filtering and/or other types of signal alterations. The vibration signature may instead be a combination of vibration signals from the vibration detector 107 that are detected at different times in response to different types of vibrations that are injected by the vibration injector 101 at different times.

The vibration detector 107 may be positioned in a fixed relation with respect to the pottery shard station 103 so as to ensure that the separation distance between the unidentified pottery shard 105 and the vibration detector 107 is maintained constant. For example, the vibration detector 107 may be gently placed in contact with a surface of the unidentified pottery shard 105 or at a fixed distance therefrom.

Figures 3, 4:
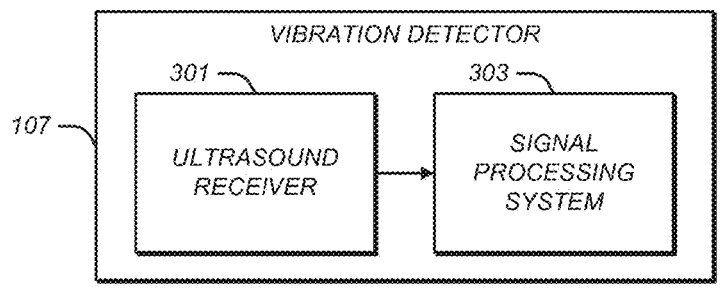
FIG. 3 illustrates an example of the vibration detector illustrated in FIG. 1 that detects ultrasound vibration signatures.
FIG. 4 illustrates an example of the known pottery shard database illustrated in FIG. 1.

FIG. 3 illustrates an example of the vibration detector 107 illustrated in FIG. 1 that detects ultrasound vibration signatures. As illustrated in FIG. 3, the vibration detector 107 may include an ultrasound receiver 301 and, optionally, a signal processing system 303 that may be configured to extract one or more signals of interest from the ultrasound receiver 301 and/or to remove one or more signals that may not be of interest. The ultrasound receiver 301 may be placed gently in contact with the unidentified pottery shard 105 or spaced a fixed distance from it.

A high speed, high resolution video camera may instead be used as the vibration detector 107, with post-capture-image processing that extracts the vibration signature from the series of video images. The vibration may also be recorded by a recording device, like a mobile phone, and be played back later for analysis and interpretation.

The vibration detector 107 may include a digital or analog storage device that stores and indexes the vibration signature(s) that are detected.

One example of a machine that may be used for both the vibration injector 101 and the vibration detector 107 is the portable ultrasound machine by Onetech Medical Equipment Co, LTD, model number B19, 2017.

The vibration signature comparator 109 may be configured to compare vibration signatures detected by the vibration detector 107 from the unidentified pottery shard 105 with vibration signatures of multiple identified pottery shards having one or more known characteristics. The vibration signatures of the multiple identified pottery shards may be contained in the known pottery shard database 111.

The vibration signature comparator 109 may be implemented in whole or in part by a mobile or stationary computer connected to the vibration detector 107 with software that is configured to perform the functions that are described herein. The connection may be a wired connection, such as through a port, such as a USB port, and/or a wireless connection, such as a connection using Bluetooth or Wi-Fi.

The vibration signature comparator 109 may be configured to flag one or more of the identified pottery shards in the known pottery shard database 111 that have vibration signatures that are similar to a detected vibration signature of the unidentified pottery shard 105.

Any algorithm may be used to determine when the vibration signature of the unidentified pottery shard 105 is similar to the vibration signature(s) of identified pottery shards. When the vibration signature is a waveform, the algorithm may analyze the waveform by using Forced Vibrational Analysis, which may include time analysis, amplitude analysis, dampening analysis, frequency analysis, or any combination of these. The analysis may be based on a single degree of freedom analysis, or multi degrees of freedom analysis. See also "*Basics of Structural Vibrational Testing and Analysis*," by Taylor, James and *The Vibration Analysis Handbook*. Vibration Consultants, $2^{nd}$ Edition, 2003.

An example of the vibration signature comparator 109 is the B&K Dactron Photon+4ch DC-84 KHz Dynamic Signal Analyzer and the PHOTON+DYNAMIC SIGNAL ANALYZER by Bruel & Kjaer." See also CoCo-80X Dynamic Signal Analyzer, Crystal Instruments, 2370 Owen Street, Santa Clara, Calif. 95054.

FIG. 4 illustrates an example of the known shard database illustrated in FIG. 1. As illustrated in FIG. 4, the known shard database may include a record for each of several different identified pottery shards that have one or more known characteristics. Although only two identified pottery shards are illustrated in FIG. 4, it is to be understood that the known shard database may have many more, such as dozens, hundreds, or even thousands of identified pottery shards.

Each identified pottery shard record in the known pottery shard database may contain several different fields of information. For example, and as illustrated in FIG. 4, each record may contain information that identifies the identified pottery shard, such as an image of the identified pottery shard. The identification information may instead or in addition include a unique ID code for the known pottery shard and/or other information about it, such as its weight, color, size, density, curvature, material, and/or shape.

For each identified pottery shard, the record may also contain information that identifies the age and creation location of the identified pottery shard that has previously been determined. These determinations may have been made using any technique, such as any of the techniques described in the Background section above or using the pottery shard analyzer illustrated in FIG. 1 and discussed herein.

Each record may also contain a vibration signature of the identified pottery shard. This signature may be obtained under conditions that are identical or substantially the same as the conditions under which the vibration signature of the unidentified pottery shard 105 is obtained. One approach, for example, would be to obtain the vibration signatures of the identified pottery shards using the same pottery shard analyzer that is used to obtain the vibration signature of the unidentified pottery shard 105, or an analyzer that is the same or substantially similar. This may eliminate variations in vibration signatures that are due to differences in the analyzers that are used.

The vibration signatures that are stored in the known pottery shard database 111 may be in any form. For example, they may be stored in the same form as the form of the vibration signature that is obtained for the unidentified pottery shard 105. That form may be a recorded analog signal or a digital file containing a digitized version of that analog signal. The vibration signatures of both the unidentified pottery shard 105 and the identified pottery shards may instead first undergo various types of signal processing before they are compared, such as filtering. The signal signature may be either a continuous segment of the vibration or may time-separated portions.

The records in the known pottery shard database 111 may be supplemented with additional records about additional known pottery shards, following which an updated comparison may be made by the vibration signature comparator 109.

The known pottery shard database 111 may be stored in any type of device, such as a hard disk drive or a flash drive. The known pottery shard database 111 may be at any location, i.e., not necessarily at the location of the other components of the pottery shard analyzer, such as in a server on the Internet that is accessible to the vibration signature comparator 109. The vibration signature comparator 109 may itself be stored at a location that is separate from other components of the part of shard analyzer, such as the same or a different server on the Internet.

The vibration signature comparator 109 may be configured to output an identification of the known pottery shards that have been determined to have similar vibration signatures, including the information in the database that identifies the known pottery shard (e.g., its image and ID) and the identification information about that known pottery shard, such as its age and creation location. If multiple matching known pottery shards are located, but the known information about them is not identical, all of the variations in this known information may also be outputted. The output may be in any form or forms, such as printed, displayed, or delivered to another computer.

The vibration signature comparator 109 may also be configured to adjust the algorithm that is used to determine similarity between the vibration signature of the unidentified pottery shard 105 and the vibration signatures of the known pottery shards in the database 111. For example, adjustments may be made to make the determination of similarity more stringent or relaxed. An adjustment making the determination more stringent may be made when the number of matches is very large. Conversely, an adjustment making the determination more relaxed may be made when the number of matches is very small. These adjustments may be automatically made by the vibration signature comparator 109 based on the size of the matching signatures and/or any other criteria.

The vibration signature comparator 109 may be configured to automatically make adjustments to its comparison algorithm to compensate for apparent differences between the unidentified pottery shard 105 and each of the known pottery shards in the known pottery shard database 111, such as differences in size, shape, and/or weight. Since shards may be of different sizes, in order for the signatures to be comparable between different shards, a standardized method of recording may be instituted. The recording may be taken at a standard distance from the vibration injection source, such as 1 cm. Multiple or single recordings may be taken, either simultaneously or sequentially.

Figure 5:
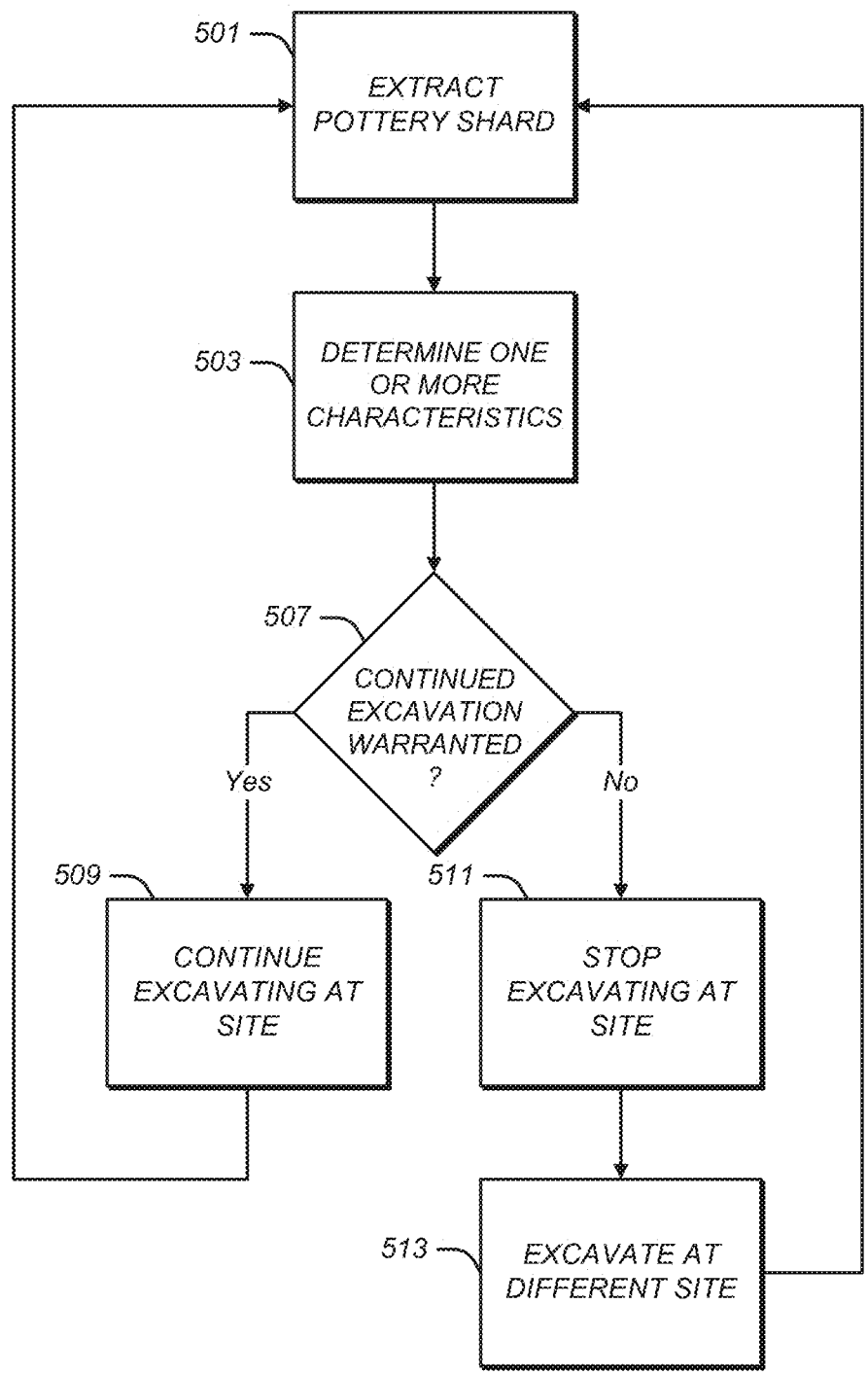
FIG. 5 illustrates an example of a method of excavating an archeological site.

FIG. 5 illustrates an example of a method of excavating an archeological site. As illustrated in FIG. 5, the method may include an extract pottery shard step 501, a determine one or more characteristics step 503, a continued excavation warranted? decision step 507, a continue excavating at site step 509, a stop excavating at site step 511, and an excavate at different site step 513.

The extract pottery shard step 501 may include excavation at a particular site. During the extract pottery shard step 501, the unidentified pottery shard 105 may be observed and extracted. Dirt and other extraneous material surrounding the unidentified pottery shard 105 may be removed before its vibration signature is extracted.

The determine one or more characteristics step 503 may then determine one or more characteristics of the extracted and unidentified pottery shard 105, such as its age and location of creation, utilizing any method, such as any of the variations of the pottery shard analyzer illustrated in FIG. 1 and its uses discussed above. This determination may be made in real time during the excavation, either on the excavation site or nearby.

The continued excavation warranted? decision step 507 may then determine whether continued excavation at the site is warranted based on the determined characteristics of the extracted and now identified pottery shard 105. For example, a subway extension construction in Rome may encounter potential archeologically important sites with foundation stones and shards of pottery. Typically, construction may have to stop to allow Archaeologists to examine the site. However, a quick onsite analysis of the pottery by one of the methods disclosed in this application may suggest that the site is from the 18$^{th}$ century and thus not an archaeological important site. The construction can then go on without undue and expensive delays.

If continued excavation is determined to be warranted, continued excavation at the site may take place, as reflected by the continued excavation at site step 509. During the continued excavation, additional pottery shards may be uncovered extracted, and the process that has just been described may be repeated in connection with one or more of these additional pottery shard as a means of excavation at the site is continues to be warranted.

If continued excavation is determined not to be warranted, on the other hand, excavation at the site may stop, as reflected by the stop excavation at site step 511. Excavation may then begin or continue at a different site, as reflected by the excavate at different site step 513. Pottery shards that are uncovered at the different site may similarly be analyzed for their characteristics, the results of which may similarly be used to determine whether excavation at the different site should continue.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/ or advantages. These also include embodiments in which the components and/or steps are arranged and/or ordered differently.

For example, although the discussions thus far involve pottery shards, the approaches that have been discussed can also be used to analyze whole or intact pottery, not limited to only fragments of pottery, like shards. As such, the technique can analyze pottery, not only in excavation, but in museums or during a commercial auction to validate the identity of an antique pottery. In addition to pottery shards, the technique can also be used to analyze other archaeological artifacts, like arrow heads. Arrow heads vibrate based on their metal content, which often reflect the local ores where the metals are harvested. In addition to the applications above, the vibration technique can also be used to analyze materials which are not necessary antique. For example, elephants and rhinoceros are often killed for their horns and tusks. Part of the global protection strategy for these animals is to prohibit the sales of objects made from these prohibited tusks and horns. However, when cut and polished, these horns and tusks can be difficult to distinguish from ox horns or bones, which may be legal. There is no easy visual test to differentiate among them, and it relies upon experts' visual inspection and possible DNA analysis. However, experts may be limited in the world and not completely accurate, and DNA analysis is expensive and time-consuming, thus not a realistic option when police are walking around markets in the Third World looking for elephant and rhino traffickers. Since elephant tusks and rhino horns have different density from ox bones, the vibration technique can be used to differentiate among them.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A pottery shard analyzer for determining one or more unknown characteristics of an unidentified pottery shard comprising:
   a vibration injector that causes the unidentified pottery shard to vibrate with a vibration signature that is dependent on the one or more characteristics of the unidentified pottery shard;
   a vibration detector that detects and extracts the vibration signature from the vibration of the unidentified pottery shard caused by the vibration injector; and
   a vibration signature comparator that:
   compares the detected vibration signature of the unidentified pottery shard with vibration signatures of multiple identified pottery shards having one or more known characteristics; and
   flags one or more of the identified pottery shards that have vibration signatures that match the vibration signature of the unidentified pottery shard,
   wherein:
      the vibration injector causes the unidentified pottery shard to vibrate at multiple different frequencies either simultaneously or sequentially;
      the vibration detector detects the vibration signature of the unidentified pottery at each of the multiple different frequencies; and
      the vibration signature comparator:
      compares the detected vibration signature of the unidentified pottery shard at each of the multiple different frequencies with vibration signatures of the multiple identified pottery shards at each of the multiple different frequencies; and
      flags one or more of the identified pottery shards that have vibration signatures at the multiple different frequencies that match the vibration signature of the unidentified pottery shard at the multiple different frequencies.

2. The pottery shard analyzer of claim 1 wherein the vibration signature comparator outputs the one or more characteristics of the flagged pottery shards.

3. The pottery shard analyzer of claim 1 wherein the vibration injector includes an ultrasound transmitter and the vibration detector include an ultrasound receiver.

4. The pottery shard analyzer of claim 1 wherein one of the characteristics is an age of the pottery shard.

5. The pottery shard analyzer of claim 1 wherein one of the characteristics is a geographic location where the pottery shard was made.

6. The pottery shard analyzer of claim 5 wherein another of the characteristics is an age of the pottery shard.

7. The pottery shard analyzer of claim 1 wherein the vibration signature comparator uses a correlation function to make the comparison.

8. The pottery shard analyzer of claim 1 further comprising a database of vibration signatures of the identified pottery shards.

9. The pottery shard analyzer of claim 1 wherein the vibration signatures of the unidentified and identified pottery shards are obtained under the same conditions.

10. The pottery shard analyzer of claim 9 wherein one of the same conditions is a separation distance between the vibration injector and the pottery shard.

11. A method of excavating a first archeological site comprising:
   extracting an unidentified pottery shard during the excavating having one or more unknown characteristics;
   using the pottery shard analyzer of claim 1 to determine the one or more unknown characteristics; and
   deciding whether the determined one or more characteristics warrant continued excavation at the first archeological site;
   if the determined one or more characteristics warrant continued excavation at the first archeological site, continuing to excavate at the first archeological site; and
   if the determined one or more characteristics do not warrant continued excavation at the first archeological site, not continuing to excavate at the first archeological site.

12. The method of excavating of claim 11 further comprising excavating at a second archeological site if the determined one or more characteristics do not warrant continued excavation at the first archeological site.

13. The method of excavating of claim 11 wherein the vibration signature comparator in the pottery shard analyzer outputs the one or more characteristics of the flagged pottery shards.

14. The method of excavating of claim 11 wherein the vibration injector in the pottery shard analyzer includes an ultrasound transmitter and the vibration detector include an ultrasound receiver.

15. The method of excavating of claim 11 wherein one of the characteristics of the pottery shard analyzer is an age of the pottery shard.

16. The method of excavating of claim 11 wherein one of the characteristics is an geographic location where the pottery shard was made.

17. The method of excavating of claim 16 wherein another of the characteristics is an age of the pottery shard.

18. The method of excavating of claim 11 wherein the vibration signature comparator in the pottery shard analyzer uses a correlation function to make the comparison.

19. The method of excavating of claim 11 wherein the pottery shard analyzer further comprises a database of vibration signatures of the identified pottery shards.

20. The method of excavating of claim 11 wherein the vibration signatures of the unidentified and identified pottery shards are obtained under the same conditions.

21. The method of excavating of claim 20 wherein one of the same conditions is a separation distance between the vibration injector and the pottery shard.

* * * * *